US012723081B2

(12) United States Patent
Thomas et al.

(10) Patent No.: US 12,723,081 B2
(45) Date of Patent: Sep. 1, 2026

(54) IN SITU THIOL-MALEIMIDE CROSSLINKED HYDROGEL FOR IMMUNE CHECKPOINT BLOCKADE DELIVERY

(71) Applicant: GEORGIA TECH RESEARCH CORPORATION, Atlanta, GA (US)

(72) Inventors: Susan Napier Thomas, Atlanta, GA (US); Jihoon Kim, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 755 days.

(21) Appl. No.: 18/015,675

(22) PCT Filed: Jul. 13, 2021

(86) PCT No.: PCT/US2021/041419

§ 371 (c)(1),
(2) Date: Jan. 11, 2023

(87) PCT Pub. No.: WO2022/015723

PCT Pub. Date: Jan. 20, 2022

(65) Prior Publication Data

US 2023/0257463 A1 Aug. 17, 2023

Related U.S. Application Data

(60) Provisional application No. 63/051,107, filed on Jul. 13, 2020.

(51) Int. Cl.

| | |
|---|---|
| ***C07K 16/28*** | (2006.01) |
| ***A61K 9/06*** | (2006.01) |
| ***A61K 39/00*** | (2006.01) |
| ***A61K 47/10*** | (2017.01) |
| ***A61P 35/00*** | (2006.01) |
| ***C08G 65/333*** | (2006.01) |
| ***C08G 65/334*** | (2006.01) |
| ***C08J 3/075*** | (2006.01) |

(52) U.S. Cl.

CPC ............ *C07K 16/2818* (2013.01); *A61K 9/06* (2013.01); *A61K 47/10* (2013.01); *A61P 35/00* (2018.01); *C08G 65/33306* (2013.01); *C08G 65/334* (2013.01); *C08J 3/075* (2013.01); *A61K 2039/505* (2013.01); *C08G 2650/58* (2013.01); *C08J 2371/02* (2013.01)

(58) Field of Classification Search

CPC .... A61K 47/34; A61K 47/6903; A61K 47/10; C08G 65/32

See application file for complete search history.

(56) References Cited

U.S. PATENT DOCUMENTS

| | | | | |
|---|---|---|---|---|
| 6,638,621 | B2 * | 10/2003 | Anderson | A61K 9/1274 424/422 |
| 9,855,317 | B2 * | 1/2018 | Bright | A61B 18/1492 |
| 2008/0076852 | A1 | 3/2008 | Smith et al. | |
| 2013/0330826 | A1 * | 12/2013 | Kim | A61K 9/0019 530/358 |
| 2020/0113816 | A1 | 4/2020 | Bellan | |
| 2020/0121598 | A1 | 4/2020 | Domb et al. | |
| 2020/0171461 | A1 | 6/2020 | Sakikawa et al. | |
| 2021/0283312 | A1 * | 9/2021 | Bierman | A61L 27/34 |

FOREIGN PATENT DOCUMENTS

| | | | | |
|---|---|---|---|---|
| WO | 2012/081799 | A1 | 6/2012 | |
| WO | WO-2016037180 | A1 * | 3/2016 | A61K 47/20 |
| WO | 2018078620 | A1 | 5/2018 | |
| WO | 2018/198076 | A1 | 11/2018 | |
| WO | 2019/048714 | A2 | 3/2019 | |
| WO | WO-2019210209 | A1 * | 10/2019 | A61L 27/56 |
| WO | 2020/019022 | A1 | 1/2020 | |

OTHER PUBLICATIONS

Bolu et al (Molecules, 2018, vol. 23, 26 pages) (Year: 2018).*
Rosendhal et al (Bioconjugate Chemistry, 2005, vol. 16, pp. 200-207) (Year: 2005).*
Harui et al (Cancer Immunology, Immunotherapy, ePub Apr. 24, 2020, vol. 69, pp. 1737-1749) (Year: 2020).*
Baxi et al (BMJ, 2018, vol. 360, k793, 13 pages). (Year: 2018).*
Extended European Search Report received in 21842321.8 mailed Jul. 26, 2024.
Nie et al: "Production of heparin-functionalized hydrogels for the development of responsive and controlled growth factor delivery systems", Journal of Controlled Release, Elsevier, Amsterdam, NL, vol. 122, No. 3, Sep. 18, 2007, pp. 287-296, XP022336560, ISSN: 0168-3659, DOI: 10.1016/J.JCONREL.2007.04.019.
International Search Report and Written Opinion received in PCT/US2021/041419 mailed Nov. 15, 2021, 12 pages.
International Preliminary Report on Patentability issued Application PCT/US2021/041419, dated Jan. 26, 2023.
Francis, D.M.; Thomas, S.N. Progress and opportunities for enhancing the delivery and efficacy of checkpoint inhibitors for cancer immunotherapy. Adv. Drug Deliver. Rev. 2017, 114, 33-42.
Ribas, A.;Wolchok, J.D. Cancer immunotherapy using checkpoint blockade. Science 2018, 359, 1350-1355.
Egen, J.G.; Kuhns, M.S.; Allison, J.P. CTLA-4: New insights into its biological function and use in tumor immunotherapy. Nat. Immunol. 2002, 3, 611-618.
Alsaab, H.O.; Sau, S.; Alzhrani, R.; Tatiparti, K.; Bhise, K.; Kashaw, S.K.; Iyer, A.K. PD-1 and PD-L1 Checkpoint Signaling Inhibition for Cancer Immunotherapy: Mechanism, Combinations, and Clinical Outcome. Front. Pharmacol. 2017, 8, 561.

(Continued)

*Primary Examiner* — Karen A. Canella

(74) *Attorney, Agent, or Firm* — Meunier Carlin & Curfman LLC

(57) ABSTRACT

Disclosed are hydrogel compositions that can be used to deliver therapeutic agents, including therapeutic proteins, to patients in need thereof. In an embodiment, the therapeutic agent is an immune checkpoint blockade antibody, and the hydrogel is a thermoresponsive polymer crosslinked with a hydrophilic polymer.

20 Claims, 8 Drawing Sheets

(56) References Cited

OTHER PUBLICATIONS

Francis, D.M.; Manspeaker, M.; Schudel, A.; Sestito, L.F.; O'Melia, M.J.; Kissick, H.T.; Pollack, B.P.; Waller, E.K.; Thomas, S.N. Blockade of immune checkpoints in lymph nodes through locoregional delivery augments cancer immunotherapy. Sci. Transl. Med. 2020, 12, eaay3575.
Crittenden, M.R.; Thanarajasingam, U.; Vile, R.G.; Gough, M.J. Intratumoral immunotherapy: Using the tumour against itself. Immunology 2005, 114, 11-22.
Marabelle, A.; Kohrt, H.; Caux, C.; Levy, R. Intratumoral Immunization: A New Paradigm for Cancer Therapy. Clin. Cancer Res. 2014, 20, 1747-1756.
Engelhard, V.H.; Rodriguez, A.B.; Mauldin, I.S.; Woods, A.N.; Peske, J.D.; Slingluff, C.L., Jr. Immune Cell Infiltration and Tertiary Lymphoid Structures as Determinants of Antitumor Immunity. J. Immunol. 2018, 200, 432-442.
Joshi, N.S.; Akama-Garren, E.H.; Lu, Y.; Lee, D.-Y.; Chang, G.P.; Li, A.; DuPage, M.; Tammela, T.; Kerper, N.R.; Farago, A.F.; et al. Regulatory T Cells in Tumor-Associated Tertiary Lymphoid Structures Suppress Anti-tumor T Cell Responses. Immunity 2015, 43, 579-590.
Mohamed, L.; Elsaka, A.; Zamzam, Y.; Elkady, A. Tumor Infiltrating Lymphocytes and Tertiary Lymphoid Structure as Prognostic and Predictive Factor for Neoadjuvant Chemotherapy in Stage II & III Breast Cancer. Arch. Can. Res. 2018, 6, 17.
Cui, Y.; Cui, P.; Chen, B.; Li, S.; Guan, H. Monoclonal antibodies: Formulations of marketed products and recent advances in novel delivery system. Drug Dev. Ind. Pharm. 2017, 43, 519-530.
Bittner, B.; Richter, W.F.; Hourcade-Potelleret, F.; McIntyre, C.; Herting, F.; Zepeda, M.L.; Schmidt, J. Development of a Subcutaneous Formulation for Trastuzumab-Nonclinical and Clinical Bridging Approach to the Approved Intravenous Dosing Regimen. Arzneimittelforschung 2012, 62, 401-409.
Jackisch, C.; Muller, V.; Maintz, C.; Hell, S.; Ataseven, B. Subcutaneous Administration of Monoclonal Antibodies in Oncology. Geburtsh Frauenheilkd. 2014, 74, 343-349.
Chen, Q.; Wang, C.; Chen, G.; Hu, Q.; Gu, Z. Delivery Strategies for Immune Checkpoint Blockade. Adv. Healthc. Mater. 2018, 7, 1800424.
Kagan, L.; Turner, M.R.; Balu-Iyer, S.V.; Mager, D.E. Subcutaneous Absorption of Monoclonal Antibodies: Role of Dose, Site of Injection, and Injection Volume on Rituximab Pharmacokinetics in Rats. Pharm. Res. 2012, 29, 490-499. [.
Bobo, D.; Robinson, K.J.; Islam, J.; Thurecht, K.J.; Corrie, S.R. Nanoparticle-Based Medicines: A Review of FDA-Approved Materials and Clinical Trials to Date. Pharm. Res. 2016, 33, 2373-2387.
Li, J.; Mooney, D.J. Designing hydrogels for controlled drug delivery. Nat. Rev. Mater. 2016, 1, 16071.
Prausnitz, M.R. Engineering Microneedle Patches for Vaccination and Drug Delivery to Skin. Annu. Rev. Chem. Biomol. Eng. 2017, 8, 177-200.
Nam, J.; Son, S.; Park, K.S.; Zou, W.; Shea, L.D.; Moon, J.J. Cancer nanomedicine for combination cancer immunotherapy. Nat. Rev. Mater. 2019, 4, 398-414.
Kim, J.; Manspeaker, M.P.; Thomas, S.N. Augmenting the synergies of chemotherapy and immunotherapy through drug delivery. Acta Biomater. 2019, 88, 1-14.
Wang, C.; Sun, W.; Wright, G.; Wang, A.Z.; Gu, Z. Inflammation-Triggered Cancer Immunotherapy by Programmed Delivery of CpG and Anti-PD1 Antibody. Adv. Mater. 2016, 28, 8912-8920.
Yu, S.; Wang, C.; Yu, J.; Wang, J.; Lu, Y.; Zhang, Y.; Zhang, X.; Hu, Q.; Sun, W.; He, C.; et al. Injectable Bioresponsive Gel Depot for Enhanced Immune Checkpoint Blockade. Adv. Mater. 2018, 30, 1801527.
Ruan, H.; Hu, Q.; Wen, D.; Chen, Q.; Chen, G.; Lu, Y.; Wang, J.; Cheng, H.; Lu, W.; Gu, Z. A Dual-Bioresponsive Drug-Delivery Depot for Combination of Epigenetic Modulation and Immune Checkpoint Blockade. Adv. Mater. 2019, 31, 1806957.
Zhang, L.; Zhou, J.; Hu, L.; Han, X.; Zou, X.; Chen, Q.; Chen, Y.; Liu, Z.; Wang, C. In Situ Formed Fibrin Scaffold with Cyclophosphamide to Synergize with Immune Checkpoint Blockade for Inhibition of Cancer Recurrence after Surgery. Adv. Funct. Mater. 2019, 1906922.
Wang, C.; Wang, J.; Zhang, X.; Yu, S.; Wen, D.; Hu, Q.; Ye, Y.; Bomba, H.; Hu, X.; Liu, Z.; et al. In situ formed reactive oxygen species-responsive scaffold with gemcitabine and checkpoint inhibitor for combination therapy. Sci. Transl. Med. 2018, 10, eaan3682.
Park, C.G.; Hartl, C.A.; Schmid, D.; Carmona, E.M.; Kim, H.-J.; Goldberg, M.S. Blockade of immune checkpoints in lymph nodes through locoregional delivery augments cancer immunotherapy. Sci. Transl. Med. 2018, 10, eaar1916.
Ren, L.; Lim, Y.T. Degradation-Regulatable Architectured Implantable Macroporous Scaffold for the Spatiotemporal Modulation of Immunosuppressive Microenvironment and Enhanced Combination Cancer Immunotherapy. Adv. Funct. Mater. 2018, 28, 1804490.
Wang, C.; Ye, Y.; Hochu, G.M.; Sadeghifar, H.; Gu, Z. Enhanced Cancer Immunotherapy by Microneedle Patch-Assisted Delivery of Anti-PD1 Antibody. Nano Lett. 2016, 16, 2334-2340.
Ye, Y.; Wang, J.; Hu, Q.; Hochu, G.M.; Xin, H.; Wang, C.; Gu, Z. Synergistic Transcutaneous Immunotherapy Enhances Antitumor Immune Responses through Delivery of Checkpoint Inhibitors. ACS Nano 2016, 10, 8956-8963.
Schmid, D.; Park, C.G.; Hartl, C.A.; Subedi, N.; Cartwright, A.N.; Puerto, R.B.; Zheng, Y.; Maiarana, J.; Freeman, G.J. ;Wucherpfennig, K.W.; et al. T cell-targeting nanoparticles focus delivery of immunotherapy to improve antitumor immunity. Nat. Commun. 2017, 8, 1747.
Du, Y.; Liang, X.; Li, Y.; Sun, T.; Jin, Z.; Xue, H.; Tian, J. Nuclear and Fluorescent Labeled PD-1-Liposome-DOX-64 Cu/IRDye800CW Allows Improved Breast Tumor Targeted Imaging and Therapy. Mol. Pharm. 2017, 14, 3978-3986.
Du, Y.; Liang, X.; Li, Y.; Sun, T.; Xue, H.; Jin, Z.; Tian, J. Liposomal nanohybrid cerasomes targeted to PD-L1 enable dualmodality imaging and improve antitumor treatments. Cancer Lett. 2018, 414, 230-238.
Kim, J.; Lee, Y.; Singha, K.; Kim, H.W.; Shin, J.H.; Jo, S.; Han, D.-K.; Kim, W.J. NONOates-Polyethylenimine Hydrogel for Controlled Nitric Oxide Release and Cell Proliferation Modulation. Bioconjugate Chem. 2011, 22, 1031-1038.
Lee, D.; Lee, Y.M.; Kim, J.; Lee, M.K.; Kim, W.J. Enhanced tumor-targeted gene delivery by bioreducible polyethylenimine tethering EGFR divalent ligands. Biomater. Sci. 2015, 3, 1096-1104.
He, C.; Kim, S.W.; Lee, D.S. In situ gelling stimuli-sensitive block copolymer hydrogels for drug delivery. J. Control. Release 2008, 127, 189-207.
Hu, W.; Wang, Z.; Xiao, Y.; Zhang, S.; Wang, J. Advances in crosslinking strategies of biomedical hydrogels. Biomater. Sci. 2019, 7, 843-855.

* cited by examiner

IN SITU THIOL-MALEIMIDE CROSSLINKED HYDROGEL FOR IMMUNE CHECKPOINT BLOCKADE DELIVERY

CROSS-REFERENCE TO RELATED APPLICATION

This application is a national stage application filed under 35 U.S.C. § 371 from PCT/US2021/041419 filed Jul. 13, 2021, which claims priority to and the benefit of U.S. Provisional Application 63/051,107, filed Jul. 13, 2020, the contents of which are hereby incorporated in their entirety.

ACKNOWLEDGEMENT OF GOVERNMENT SUPPORT

This invention was made with government support under grant number R01CA207619 awarded by the National Institutes of Health, and under grant number W81XWH-16-1-0518 awarded by the United States Department of Defense. The government has certain rights in the invention.

FIELD OF THE INVENTION

The invention relates to hydrogel compositions containing therapeutic agents, for example immune checkpoint blockade antibodies. The invention relates to methods of treating diseases, including cancer, to by administering hydrogel compositions containing therapeutic agents, for example immune checkpoint blockade antibodies.

BACKGROUND

Cancers remain to have a major impact on society both in the US and across the world despite continued research. In 2018, over 1.7 million new cases of cancer were diagnosed in the US with over 600,000 people dying from the disease. In 2017, it was reported that US cancer related care costs were approximately $147.3 billion which is expected to rise due mainly in part to the aging population and costly treatment options. One of the main hurdles for improving cancer therapies and costs is the ability to completely eradicate tumors, both primary and distant metastatic cancers, as incomplete elimination is common in chemotherapies after therapy is discontinued which can lead to cancer recurrence requiring subsequent treatment. In addition, incomplete elimination can lead to increased cancer mutations leading chemotherapy to be ineffective and requiring combination of multiple therapies and/or more invasive surgical procedures. New therapy options are being widely explored to enhance long term efficacy and reduce costs, one of which is the emergence of cancer immunotherapy, where the body's own immune system is utilized.

The principle of cancer immunotherapy is based on the fact that cancers are known to form and utilize a variety of genetic and epigenetic mutations, leading to the formation of neoantigens, which can be recognized by the immune system. The adaptive immune system, composed of B and T lymphocytes has the potential to eliminate cancers due to the broad recognition of cancer neoantigens and effective cytotoxic functions, similar to the way the immune system eliminates invading pathogens like bacteria and viruses. In addition, the memory and systemic component of the immune system allows the immune system to recognize recurrent cancers many years later and metastatic cancers that have spread to distant organs. Utilization of these features is why cancer immunotherapy is a very exciting new treatment option.

Several immune checkpoint blockade monoclonal antibodies (mAb) have emerged in recent years for the treatment of melanoma and lung cancer and have garnered enormous success and excitement. These include the development of ipilimumab (Yervoy), which binds to the cytotoxic t-lymphocyte antigen-4 (CTLA-4) receptor and inhibits the suppressive function. Furthermore, pembrolizumab (Keytruda) and nivolumab (Opdivo) have been FDA approved which bind to the programmed death-1 (PD-1) receptor leading to inhibition of this pathway. Several other pathways are of interest as well including, but not limited to lymphocyte-activation gene 3 (LAG-3) and T-cell immunoglobulin and mucin-domain containing-3 (TIM-3).

Despite these successes, improvements in safety and efficacy for checkpoint inhibitor antibodies warrants further research. Currently, immune checkpoint blockade antibodies are targeted to the tumor tissue as they have been shown to restore immune cell function leading to reduced tumor burden. These therapies are administered intravenously (i.v.) leading to 100% bioavailability in the blood, however this leads to minor accumulation in the tissue of interest, in this case the tumor microenvironment (TME). Furthermore, an i.v. administration leads to accumulation in unwanted tissues including the blood rich systemic organs (lungs, liver, and kidneys). Taken together, the current i.v. administration has limited response rates (~20% in patients receiving these drugs) and unwanted immune related toxicities and side effects associated with these therapies.

T cells undergo activation in the lymphoid tissues including the spleen and hundreds of lymph nodes throughout the body. In the case of cancer, tumor neoantigen is released by dying tumor cells and subsequently drains to tumor draining lymph nodes downstream from the tumor. This neoantigen can provoke an immune response, however cancers have evolved to utilize a variety of suppressive pathways including but not limited to checkpoint pathways. When these suppressive pathways are active and bind to their ligands, T cell activation and function is dampened leading to reduced proliferation, differentiation, and can lead to reduced tumor killing function. Consequently, an anti-cancer immune response can be limited or prevented altogether as tumor specific T cells are not generated. Furthermore, when checkpoint therapy is targeted to the TME, no effect is commonly observed leading to poor response rates. One possible explanation for this is insufficient immune cell infiltration into the tumor and thus the checkpoint blockade therapy cannot activate immune T cells as they are not present. Therefore, delivery of immune checkpoint inhibitor antibodies to tumor draining lymph nodes has the potential to promote activation of T cells leading to enhanced infiltration into the TME leading to improvements in therapy. Another explanation of ineffective therapy is that tumor infiltrating immune cells are suppressed by checkpoint pathways and systemically administered therapy does not accumulate in the TME at high enough levels due to the tortuous and heterogeneous vasculature that can function improperly. Rather than target therapies to the altered TME that varies patient to patient, delivery of this therapy to the tumor draining lymph node where many immune cells reside, may successfully bind to checkpoint expressing immune cells which may then be carried into the TME where these immune cells are not suppressed and instead can effectively eliminate tumor cells.

Administration techniques outside of i.v. have emerged including intra-tumoral and cutaneous injections for various reasons. Intra-tumoral administrations are commonly used to identify tumor draining lymph nodes when planning to resect LNs that have metastatic cancers and if a high drug accumulation in the TME is desired and feasible. Cutaneous administrations, including intradermal and subcutaneous injections, are ideal for sustained delivery of antibody molecules into the blood which prolong the circulation time in vivo and to improve patient compliance have also been explored. However, neither injection scheme has focused on lymphatic drug delivery to draining lymph nodes to augment efficacy. Using a local injection in the skin, the majority of antibody molecules are cleared by the lymphatics and thus accumulate in draining lymph nodes downstream from the injection site. Improvements in safety and efficacy for checkpoint inhibitor antibodies warrants further research and more options to overcome these limitations, of which delivery platforms may provide immediate new options.

The remains a need for improved methods of treating cancers, including tumors, such as found in breast cancer. There remains a need for improved drug delivery systems for the controlled and sustained delivery of therapeutic agents to patients in need thereof. There remains a need for improved drug delivery systems for the administration of therapeutic proteins, including immune checkpoint blockade antibodies. There remains a need for injectable depot formulations that do not lead to immediate burst release of the therapeutic agent, including therapeutic proteins such as immune checkpoint blockade antibodies. There remains a need for improved depot formulations that need not be directly injected into the tumor site.

SUMMARY

In accordance with the purposes of the disclosed materials and methods, as embodied and broadly described herein, the disclosed subject matter, in one aspect, relates to compounds, compositions and methods of making and using compounds and compositions. In specific examples, discloses are methods of promoting wound healing in a patient in need thereof comprising administering to the patient a composition comprising a neonatal fibrin scaffold.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments are set forth in the descriptions below. Other features, objects, and advantages will be apparent from the description and from the claims.

BRIEF DESCRIPTION OF THE FIGURES

FIG. 6 depicts the characterization of in situ crosslinked F127/PEG hydrogel.

FIG. 7 depicts the antibody release from in situ crosslinked F127/PEG hydrogels in vivo.

FIG. 8 depicts the antitumor effects of aCTLA-4+aPD-1 antibody containing F127/PEG hydrogels in vivo.

DETAILED DESCRIPTION

Figure 1:
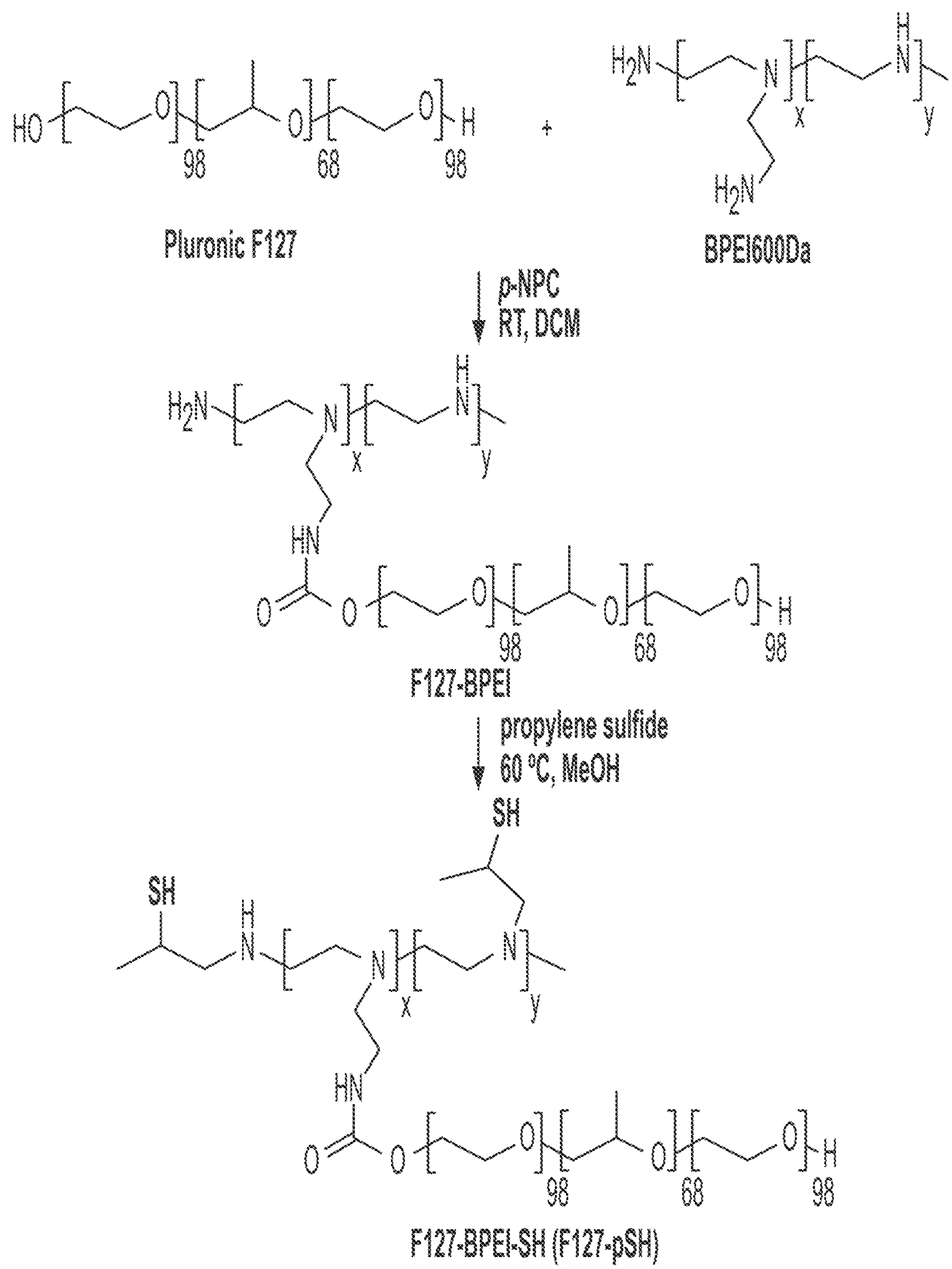
FIG. 1 depicts a synthetic method for obtaining a thiolated thermoresponsive polymer with monolinked amphiphilic polymer (crosslinked amphiphilic polymer portions are not depicted)

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes-, from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "therapeutic" generally can refer to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof.

The terms "treating" and "treatment" as used herein refer generally to obtaining a desired pharmacological and/or physiological effect. The effect may be prophylactic in terms of preventing or partially preventing a disease, symptom or condition thereof.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "active agent" or "active ingredient" refers to a component or components of a composition to which the whole or part of the effect of the composition can be attributed.

As used herein, "dose," "unit dose," or "dosage" refers to physically discrete units suitable for use in a subject, each unit containing a predetermined quantity of active agent or active ingredient without or with pharmaceutically acceptable carrier or excipient in in situ crosslinked hydrogel, calculated to produce the desired response or responses in association with its administration.

As used herein, "Administering" refers to an injection site on the subject anywhere that is upstream of the tumor-draining lymph node.

As used herein, "Antibody" refers to a glycoprotein immunoglobulin which specifically binds to an antigen and comprises at least two light and two heavy chains interconnected by disulfide bonds. The antibody is composed of a variable region and a constant region where the variable region recognizes distinct antigens and the constant region is recognized by other cells of the immune system and components of the complement system.

As used herein, "monoclonal antibody" (mAb) refers to a non-naturally occurring antibody where the primary sequences are identical leading to a single binding specificity and affinity to a particular epitope. mAbs may be produced by hybridoma, recombinant, transgenic or other techniques.

As used herein, "Cytotoxic T-lymphocyte antigen 4" (CTLA-4) refers to a transmembrane immunoinhibitory receptor found on a variety of T and B cells. CTLA4 binds to two ligands, CD80 and CD86, and has opposing function to CD28 where it prevents T cells activation.

As used herein, "Programmed death-1" (PD-1) refers to a transmembrane receptor found primarily on activated T cells with two ligands, PD-L1 and PD-L2. PD-1 restricts the function of activated T cells including the cytotoxic function.

As used herein, "Programmed death ligand-1" (PD-L1) refers to one of the two surface ligands to PD-1 and is found on a variety of hematopoietic and nonhematopoietic cells including cancer cells. PD-L1 leads to T cell suppressed activation and function following binding to PD-1.

As used herein, "Lymphocyte-activation gene 3" (LAG-3) refers to a cell surface immune checkpoint receptor molecule with many effects on T cell function.

As used herein, "T-cell immunoglobulin and mucin-domain containing-3" (TIM-3) refers to a cell surface immune checkpoint receptor molecule that mediates CD8 T cell exhaustion that has been reported to be utilized by a variety of tumor types.

As used herein, "Lymph node" (LN) refers to bean shaped structure that house the body's immune system which are scattered throughout the body. LNs filter foreign substances that travel through the lymphatic fluid and contain both T and B lymphocytes. LNs are where lymphocytes are activated against specific antigens. Tumor draining lymph nodes lie immediately downstream of tumors and undergo alterations in their structure and function, which is due to the drainage of tumor antigens and signaling molecules from the presence of the upstream tumor.

As used herein, "Lymphatics" or lymph vessels refer to a part of the lymphatic system that transport lymph in the body. Lymphatics are organized as one way vessels that help absorb interstitial fluid known as lymph from tissues and transport it to lymph nodes.

As used herein, "immune response" refers to the action of the immune system including immune cells and macromolecules produced by these cells that leads selective targeting and destruction of pathogens or cancer cells and healthy cells in the case of autoimmunity.

As used herein, "checkpoint blockade therapy" refers to the inhibition of the cytotoxic T-lymphocyte antigen 4 and/or programmed death-1 and/or T-cell immunoglobulin and mucin-domain containing-3 and/or lymphocyte-activation gene 3 pathways as well as other immune checkpoint pathways As used herein, "checkpoint inhibitor antibody" refers to the antibody to the cytotoxic T-lymphocyte antigen 4 and/or programmed death-1 and/or T-cell immunoglobulin and mucin-domain containing-3 and/or lymphocyte-activation gene 3 pathways as well as other immune checkpoint pathways As used herein, "local" refers to an administration that is in the same lymphatic tissue basin of which drains to the tumor draining lymph node.

As used herein, "T cell" refers to a lymphocyte produced by the thymus gland that resides in lymph nodes. T cells play a major role in cell-mediated immunity which is mediated by their specificity toward antigens due to their T cell receptor and cytotoxic mechanisms to eliminate infected or mutated cells. T cells play a major role in cancer immunotherapy and express both CTLA-4 and PD-1.

As used herein, "Drug delivery systems (DDSs)" refers to a pharmaceutically acceptable carrier or excipient to improve drug biodistribution and pharmacokinetic/pharmacodynamic profiles. DDSs include inorganic nanoparticles, micelles, liposomes, hydrogel, scaffold, microneedles with or without electrical devices.

As used herein, "thermosensitive polymer" indicates organic molecules to form the hydrogel which exist as a fluid form or a sol in an aqueous dispersion medium below room temperature, but undergo a phase transition upon a temperature increase into a certain range of temperature above the critical temperature, thereby forming a hydrogel without chemical crosslinks. The thermosensitive polymers include Tetronic® (T304, T904, and T1307) and Pluronic® (F127, P85, and F68) polymers that are thermosensitive block copolymer containing hydroxyl or carboxylic acid end functional groups.

As used herein, "polymers with more than three primary amines" include branched polyethyleneimines, polypropylamines, chitosan and polypeptides including poly-L-lysine that have more than three primary amines groups capable of chemically conjugated to the carboxylic acid or hydroxyl groups of thermosensitive polymers. Polymers with more than three primary amines include branched polyethyleneimines, polypropylamines, chitosan and polypeptides including poly-L-lysine.

Disclosed herein are hydrogel compositions for the delivery of therapeutics agents to a subject in need thereof. In some embodiments, the therapeutic agent is a small molecule or a therapeutic protein, including antibodies and monoclonal antibodies. In further embodiments, the therapeutic agent is one or more immune checkpoint blockade antibodies, for example a) an anti-PD-1 antibody or an antigen-binding portion thereof that binds specifically to a human PD-1; and/or (b) an anti-CTLA-4 antibody or an antigen-binding portion thereof that binds specifically to a human CTLA-4 locally; and/or (c) an anti-LAG-3 antibody or an antigen-binding portion thereof that binds specifically to a human LAG-3 locally; and/or (d) an anti-TIM-3 antibody or an antigen-binding portion thereof that binds specifically to a human TIM-3 locally; and/or (e) any other immune checkpoint antibody biologic, either whole or fragment which is based off the dosage to drug tumor draining lymph nodes in the particular patient.

In some instance, the hydrogel composition includes an immune checkpoint inhibitor, for example a PD1 blockade inhibitor and/or a CTLA-4 inhibitor. Examples include tremelimumab avelumab, ipilimumab, atezolizumab, durvalumab lambrolizumab, nivolumab, pembrolizumab, pidilizumab, and nivolumab.

In some embodiments the hydrogel composition can include a therapeutic agent including, but not limited to, to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNIS ONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

Disclosed herein are hydrogel compositions obtained by crosslinking branched or multi-arm electrophilic, hydrophilic polymers with thiolated thermoresponsive polymers. Suitable hydrophilic polymers include polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof.

The molecular weight of the hydrophilic polymer (prior to crosslinking) can be from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000 (Daltons).

In certain embodiments, the hydrophilic polymer is a polyethylene glycol, i.e., PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, from 40,000-60,000, from 1,000-10,000, from 1,000-7,500, from 2,500-7,500, or from 5,000-25,000 (Daltons).

As used herein, a multi-arm polymer describes a polymer having a central core with at least three polymers covalently attached thereto. Multi-arm polymers can have 3, 4, 5, 6, 7, 8 or more polymer arms. Preferred multi-arm polymers, as defined above, include those with 4 arms. Generally, all of the polymers attached to the core are the same, but in some instances different hydrophilic polymers, as defined above, can be used. Suitable cores include those derived from polyols, including glycerol (3-arm), pentaerythritol (4-arm), tetraglycerol (6-arm), and hexaglycerol (8-arm). A particularly preferred polymer is a 4-arm PEG, having a total molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000 (Daltons).

Suitable core groups can be derived from a polyol such as glycerol, pentaerythritol, sorbitol, mannitol, tetraglycerol, and hexaglycerol. In some instances, the core can have the general structure:

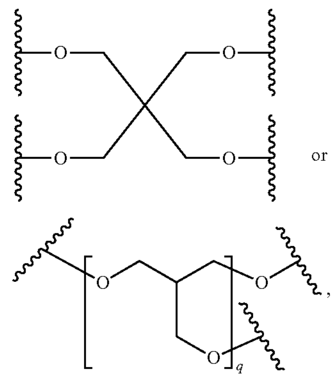

or , wherein q is any integer, for instance 1, 2, 3, 4, 5, 6, 7, 8, 9, or 10 and ⌇ represents a link to a hydrophilic polymer, as described above. Other suitable polyols include carbohydrates, including monosaccharides and di-saccharides, such as glucose, xylose, mannose, galactose, sucrose, maltose, trehalose and fructose, and cyclic polyols like cyclopropane-1,2,3-triol, cyclobutane-1,2,3,4-tetraol, cyclopentane-1,2,3,4-tetraol, cyclopentane-1,2,3,4,5-pentaol, cyclohexane-1,2,4,5-tetraol, cyclohexane-1,2,3,4,5,6-hexaol, and the like.

In certain embodiments, the electrophilic polymer is a compound of Formula (1):

[Formula (1)]

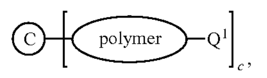

wherein encircled C represents a core, polymer represents a hydrophilic polymer as defined above, c is an integer from 3-10, 3-8, 3-6, 3-5, 4-5, 4-6, or 3-4, and $Q^1$ represents an electrophilic group.

In some instances, $Q^1$ has the formula:

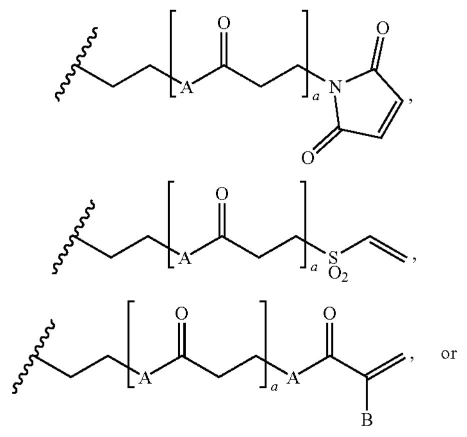

, , or

-continued

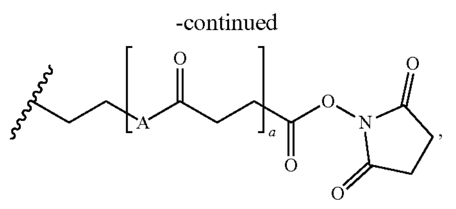

wherein A is independently selected from O or NH, a is independently selected from 0 or 1, B is selected from hydrogen or methyl, and ⌇ represents a link to a hydrophilic polymer, as described above.

In certain preferred embodiments, c is 4, the hydrophilic polymer is a polyethylene glycol, and $Q^1$ is:

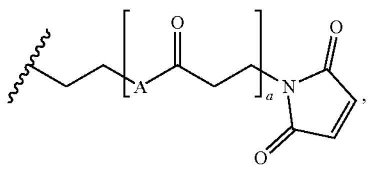

wherein A is NH, and a is 1.

The thermoresponsive polymer can include an amphiphilic polymer, e.g., a polymer containing both hydrophilic and hydrophobic domains. The amphiphilic polymer preferably contains one or more hydroxyl groups, for instance two hydroxyl groups, three hydroxyl group, four hydroxyl groups, etc. Exemplary hydrophilic polymers include poly(ethylene oxide)-poly(propylene oxide) block copolymers, for example poly(ethylene oxide)-poly(propylene oxide)-poly(ethylene oxide) block copolymers such as poloxamer 188 or poloxamer 407 (i.e., Pluronic F127) and ethylenediamine tetrakis(ethoxylate-block-propoxylate) tetrols, such as Tetronic 304 (T304), Tetronic 904 (T904) or Tetronic 1307 (T1307). The skilled person appreciates that poly(ethylene oxide)-poly(propylene oxide)-poly(ethylene oxide) block copolymers have two hydroxyl groups, whereas ethylenediamine tetrakis(ethoxylate-block-propoxylate) tetrol copolymers have four hydroxyl groups.

In some instances the amphiphilic polymer has the formula:

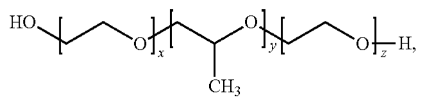

wherein x, y, and z are independently selected from 5-500. In certain embodiments x and z are the same and are selected from 10-150, from 25-150, from 50-150, from 75-150, from 100-150, from 125-150, from 10-125, from 25-125, from 50-125, from 75-125, from 10-100, from 25-100, from 50-100, or from 75-100. In certain embodiments y is selected from 10-100, from 25-100, from 50-100, from 25-75, from 50-70, or from 50-100. In some preferred embodiments, x and z are both from 75-125, and y is from 50-70.

In some instances the amphiphilic polymer has the formula:

wherein $R^t$ is in each case

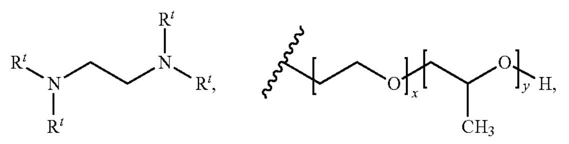

and x and y are as defined above.

The polymer having at least three primary amines can be a polyethyleneimine, polypropyleneimine, chitosan or polypeptide. A preferred polymer having at least three primary amines is polyethyleneimine ("BPEI"). BPEI can be obtained from ring-opening polymerization of aziridine. The resulting polymer can be a random distribution of primary, secondary, and tertiary amines

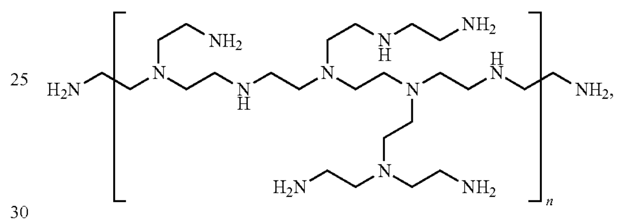

wherein n is an integer from 1-20,000. BPEI may be characterized by molecular weight, suitable MW ranges useful in the disclosed compositions include 300-25,000, 300-15,000, 300-10,000, 300-5,000, 300-2,500, or 300-2,500 (Daltons). in some embodiments, the polyethyleneimine has a molecular weight from 100-5,000, from 250-5,000, from 250-2,500, from 250-1,500, from 250-1,000, or from 250-750 (Daltons).

The amphiphilic polymer may be conjugated to a polymer with more than three primary amines using conventional bond forming reactions. In an embodiment, the amphiphilic polymer is first reacted with an activating group, and subsequently conjugated to the polymer with more than three primary amines. For example, amphiphilic polymers having hydroxyl groups may be first activated using reagents such as nitrophenyl chloroformate, and then reacted with the polymer with more than three primary amines to give the thermoresponsive polymer. Other functional groups, such as carboxylic acids, may be activated using, for example, biscarbodiimides, hydroxy succinimides, or phenyl chloroformates, and then reacted with the polymer with more than three primary amines. In other embodiments, the amphiphilic polymer includes a Michael acceptor, for instance a (meth)acrylamide or (meth)acrylate group.

The thermoresponsive polymer can include a plurality of amphiphilic polymers conjugated to a single polymer with at least three amines. In some embodiments, the thermoresponsive polymer is prepared by reacting the amphiphilic polymer and polymer with at least three primary amines in the presence of an activating group to form a covalent bond between one or more primary amines and the amphiphilic polymer. The molar ratio of polymer with at least three primary amines to the amphiphilic polymer can be from 100:1-1:1, from 50:1 to 1:1, from 25:1 to 1:1, from 10:1 to 1:1, from 20:1 to 1.05:1, from 10:1 to 1.05:1, from 7.5:1 to 1.05:1, from 5:1 to 1.05:1, from 10:1 to 2.5:1, from 10:1 to 5:1, from 15:1 to 5:1, from 12.5:1 to 7.5:1, or from 7.5:1 to 2.5:1. When the polymer with at least three primary amines is BPEI, the molar ratio of the BPEI to amphiphilic polymer (e.g., a poly(ethylene oxide)-poly(propylene oxide)-poly (ethylene oxide) block copolymers or ethylenediamine tetrakis(ethoxylate-block-propoxylate) tetrols, as described above), can be from 100:1-1:1, from 50:1 to 1:1, from 25:1 to 1:1, from 10:1 to 1:1, from 20:1 to 1.05:1, from 10:1 to 1.05:1, from 7.5:1 to 1.05:1, from 5:1 to 1.05:1, from 10:1 to 2.5:1, from 10:1 to 5:1, from 15:1 to 5:1, from 12.5:1 to 7.5:1, or from 7.5:1 to 2.5:1. When the amphiphilic polymer includes two or more hydroxyl groups, the skilled person appreciates that the reaction can produce a crosslinked product in which two or more BPEI molecules are linked via the same amphiphilic polymer (defined herein a crosslinked amphiphilic polymer). The skilled person also appreciates that depending on the reaction conditions and stoichiometry, the product can include compounds in which the amphiphilic polymer includes a single covalent bond to a BPEI molecule (defined herein as a monolinked amphiphilic polymer). A single BPEI molecule may include both crosslinked and monolinked amphiphilic polymers. The ratio of crosslinked to monolinked amphiphilic polymers can be from 100:1 to 1:100, from 100:1 to 1:1, from 100:1 to 2:1, from 50:1 to 1:1, from 25:1 to 1:1, from 10:1 to 1:1, from 5:1 to 1:1, from 10:1 to 5:1, from 20:1 to 10:1, from 20:1 to 5:1, or from 15:1 to 2.5:1.

The sol-gel transition temperature of the thermosensitive polymer can be assessed using a vial-tilting method. The thermoresponsive polymer (as a 20% w/v solution) can have a sol-gel transition temperature no greater than 26° C., no greater than 25° C., no greater than 24° C., no greater than 23° C., no greater than 22° C., no greater than 21° C., no greater than 20° C., no greater than 19° C., no greater than 18° C., or no greater than 17° C. The thermoresponsive polymer (as a 20% w/v solution) can have a gel-separation transition temperature no greater than 80° C., no greater than 75° C., no greater than 70° C., no greater than 65° C., no greater than 60° C., no greater than 55° C., no greater than 50° C., no greater than 45° C., no greater than 40° C., or no greater than 35° C.

The thermoresponsive polymer can be thiolated to give a thermoresponsive polymer having free thiol (—SH) groups. In preferred embodiments, the thermoresponsive polymer can be thiolated under conditions that no primary amines remain in the thermoresponsive polymer. Subsequent to thiolation, the thermoresponsive polymer can have from 1-20 thiol groups, from 2-20 thiol groups, from 5-20 thiol groups, from 10-20 thiol groups, from 1-10 thiol groups, from 2-10 thiol groups, from 5-10 thiol groups, from 1-7 thiol groups, from 2-7 thiol groups, from 2-5 thiol groups, or from 4-7 thiol groups. The number of thiol groups may be determined using Ellman's assay.

The thermoresponsive polymer may be thiolated by reaction with propylene sulfide. The degree of thiolation can be controlled through stoichiometry, as well as reaction time and temperature.

In certain embodiments, the hydrogels may be prepared by combining a composition including the thiolated thermoresponsive polymer with a composition including the multi-arm electrophilic, hydrophilic polymer, thereby crosslinking the components into a hydrogel. One or more therapeutic agents, including immune checkpoint blockade antibodies may be included in either, or both, compositions prior to crosslinking. In other embodiments a first composition containing a thiolated thermoresponsive polymer, a second composition containing the electrophilic polymer, and a third composition containing one or more active ingredients can be combined. Also provided here are kits containing separate thiolated thermoresponsive polymer, electrophilic polymer, and active ingredients, each in individual vials, syringes or other containers. The components may be provided as aqueous solutions or lyophilized powders The compositions containing the thiolated thermoresponsive polymer and multi-arm hydrophilic polymer can include a number of different solvents, buffers, surfactants, dispersants, emulsifiers, pH modifying agents, and combinations thereof. In preferred embodiments, the thiolated thermoresponsive polymer can be dispersed in phosphate buffer saline (PBS) at a concentration from 1-10 wt. %, from 2-10 wt. %, from 4-10 wt. %, from 1-6 wt. %, or from 2-6 wt. %. In certain embodiments, the thiolated thermoresponsive polymer is dispersed in PBS that does not contain calcium or magnesium ions. In certain embodiments, the multi-arm hydrophilic polymer can be dispersed in phosphate buffer saline (PBS) at a concentration from 1-18 wt. %, from 2-18 wt. %, from 5-15 wt. %, from 5-10 wt. %, or from 7-12 wt. %. In certain embodiments, the multi-arm hydrophilic polymer is dispersed in PBS that does not contain calcium or magnesium ions.

In certain embodiments, the components can be combined according to the molar ratio of thiol and $Q^1$ (i.e., the electrophilic group). For example, the molar ratio of the thiol to $Q^1$ group is about 1:1, although in some embodiments other ratios can be employed, for instance 1:1 to 1:2, 2:1 to 1:1, or 1.5:1 to 1:1.5.

The resulting hydrogel may be combined with water and, if desired, additional components and therapeutic agents to give a pharmaceutical composition. In some embodiments, the pharmaceutical composition will include at least 80% by weight of water, at least 85% by weight of water, at least 90% by weight of water, at least 92.5% by weight of water, at least 95% by weight of water, or at least 97.5% by weight of water. In certain embodiments, the composition will include from 80-99% by weight of water, from 85-99% by weight of water, from 90-99% by weight of water, from 92.50-99% by weight of water, from 95-99% by weight of water, from 90-97.5% by weight of water, from 92.50-97.5% by weight of water, or from 95-97.5% by weight of water. In other embodiments, the hydrogel is provided as a lyophilized powder, which can be reconstituted in a suitable aqueous vehicle prior to administration.

The hydrogels containing therapeutic agents, such as immune checkpoint blockade antibodies, can be prepared as a form of particles using conventional sizing methods, for example sieving. The particles can have an average particle size from 1 nm-1,000 μm. In some instances, the particles have a size from 10-1,000 nm, from 50-1,000 nm, from 100-1,000 nm, from 250-1,000 nm, from 500-1,000 nm, from 250 nm-750 nm, from 500 nm-1,500 nm, from 0.5 μm-500 μm, from 10 μm-500 μm, from 50 μm-500 μm, or from 100 μm-500 μm.

The composition including hydrogels as described herein can include solvents or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

In certain embodiments, the hydrogels may be lyophilized to give a powder, which may be reconstituted in water or other pharmaceutically acceptable solution for administration.

The compositions may include one or more surfactants, for example anionic, cationic, amphoteric or nonionic surfactants. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The compositions may include one or more preservatives to prevent the growth of microorganisms. Suitable preservatives include, but are not limited to, parabens, chlorobutanol, phenol, sorbic acid, thimerosal, polyhexamethylenebiguanidine (PHMB), benzalkonium chloride (BAK), stabilized oxychloro complexes (otherwise known as Purite®), phenylmercuric acetate, chlorhexidine, benzyl alcohol, and mixtures thereof.

The compositions can be buffered to a pH of 3-8 for parenteral administration upon reconstitution. Suitable buffers include, but are not limited to, phosphate buffers, acetate buffers, and citrate buffers.

The hydrogels disclosed herein may be used to treat cancer, for example cancers exhibiting solid tumors. In some instances, the cancer to be treated is breast cancer. In other embodiments, the cancer to be treated acute lymphoblastic leukemia (ALL), acute myeloid leukemia (AML), cancer in adrenocortical carcinoma, adrenal cortex cancer, AIDS-related cancers, Kaposi sarcoma, AIDS-related lymphoma, primary CNS lymphoma, anal cancer, appendix cancer, carcinoid tumors, astrocytomas, atypical teratoid/rhabdoid tumor, basal cell carcinoma, skin cancer (nonmelanoma), bile duct cancer, extrahepatic bladder cancer, bladder cancer, bone cancer (includes Ewing sarcoma and osteosarcoma and malignant fibrous histiocytoma), brain tumors, breast cancer, bronchial tumors, Burkitt lymphoma (non-Hodgkin), carcinoid tumor, cardiac (heart) tumors, atypical teratoid/rhabdoid tumor, embryonal tumors, germ cell tumors, lymphoma, primary-cervical cancer, cholangiocarcinoma, chordoma, chronic lymphocytic leukemia (CLL), chronic myelogenous leukemia (CML), chronic myeloproliferative neoplasms, colorectal cancer, colorectal cancer, craniopharyngioma, cutaneous T-cell lymphoma, ductal carcinoma in situ (DCIS), embryonal tumors, central nervous system, endometrial cancer, ependymoma, esophageal, esthesioneuroblastoma, ewing sarcoma, extracranial germ cell tumor, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastric (stomach) cancer, gastrointestinal carcinoid tumor, gastrointestinal stromal tumors (GIST), gastrointestinal stromal tumors (GIST), germ cell tumors, central nervous system, extracranial, extragonadal, ovarian testicular, gestational trophoblastic disease, gliomas, hairy cell leukemia, head and neck cancer, heart tumors, hepatocellular (liver) cancer, histiocytosis, Langerhans Cell, Hodgkin's lymphoma, hypopharyngeal cancer, intraocular melanoma, islet cell tumors, pancreatic neuroendocrine tumors, Kaposi sarcoma, kidney-langerhans cell histiocytosis, laryngeal cancer, laryngeal cancer and papillomatosis, leukemia, lip and oral cavity cancer, liver cancer (primary), lung cancer, lung cancer, lymphoma-macroglobulinemia, Waldenström-Non-Hodgkin lymphoma, male breast cancer, malignant fibrous histiocytoma of bone and osteosarcoma, melanoma, intraocular (eye), Merkel cell carcinoma, mesothelioma, malignant, mesothelioma, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (CML), myeloid leukemia, acute (AML), nasal cavity and paranasal sinus cancer, nasopharyngeal cancer, nasopharyngeal cancer, neuroblastoma, non-hodgkin lymphoma, non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), papillomatosis, paraganglioma, paraganglioma, paranasal sinus and nasal cavity cancer, parathyroid cancer, penile cancer, pharyngeal cancer, pheochromocytoma, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, retinoblastoma, rhabdomyosarcoma, salivary gland cancer, salivary gland tumors, Ewing sarcoma, Kaposi sarcoma, osteosarcoma, rhabdomyosarcoma, uterine sarcoma, vascular tumors, Sézary syndrome, skin cancer, small cell lung cancer, small intestine cancer, soft tissue sarcoma, squamous cell carcinoma, squamous neck cancer with occult primary, metastatic, stomach (gastric) cancer, stomach (gastric) cancer, T-cell lymphoma, cutaneous, testicular cancer, throat cancer, thymoma and thymic carcinoma, thyroid cancer, ureter and renal pelvis, transitional cell cancer, urethral cancer, uterine cancer, endometrial and uterine sarcoma, vaginal cancer, vaginal cancer, vascular tumors, vulvar cancer, Waldenström Macroglobulinemia, Wilms Tumor.

The hydrogels disclosed herein may be administered parenterally to a patient in need thereof. In some embodiment, the hydrogel compositions may be injected into, or directly adjacent to a tumor or cancerous cells. In other embodiments, the hydrogel compositions may be administered to a location apart from the tumor or cancerous cells, such that the hydrogel does not directly contact the tumor or cancerous cells. The hydrogel may be administered subcutaneously (i.e., underneath the epidermis, dermis, and hypodermis) or intradermally (i.e., within the dermis, between the epidermis and hypodermis). In yet other embodiments, the hydrogel compositions can be administered intramuscularly.

EXAMPLES

The following examples are for the purpose of illustration of the invention only and are not intended to limit the scope of the present invention in any manner whatsoever.

Example 1—Synthesis of Thiolated Pluronic F127 (F127-pSH)

Pluronic® F127 (10 g) in dichloromethane (70 mL) was activated with p-NPC (1.6 g) for two days, followed by precipitation under cold ethyl ether. BPEI600 Da (5 g) in dichloromethane (50 mL) was reacted with the activated F127 for two days and dialyzed with dialysis membrane (MWCO 10 kDa) against deionized water (D.W.) until yellow byproduct was not detected, followed by freezing drying. The thermosensitive sol-gel transition behaviors of resultant F127-BPEI were investigated using a vial tilting method. F127-pSH was synthesized by reacting F127-BPEI (1.6 g) in methanol (70 mL) with propylene sulfide (5 mL) at 60° C. for two days and precipitated under cold ethyl ether three times. The composition of resultant F127-BPEI and F127-pSH in $D_2O$ was confirmed by 1H nuclear magnetic resonance spectroscopy (1H NMR) with Bruker Advance 400 MHz FT-NMR.

Figure 2:
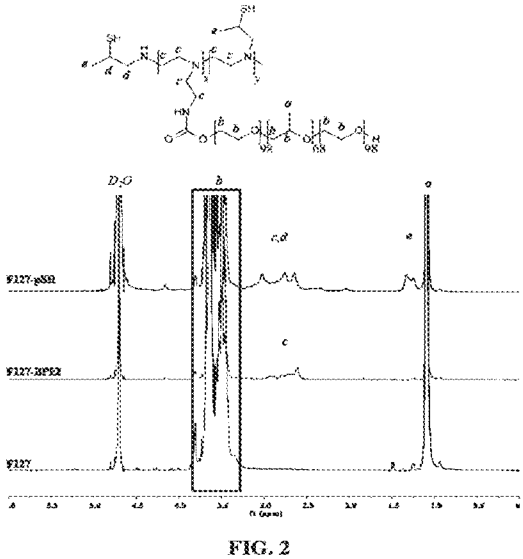
FIG. 2 depicts the $^{1}H$ NMR of F127, F127-BPE, and F127-pSH in $D_2O$ (the chemical structure does not depict the crosslinked amphiphilic polymers present).
Figure 3:
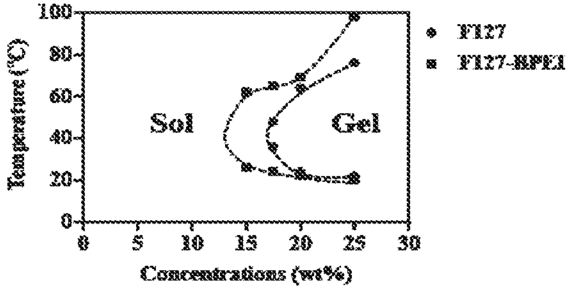
FIG. 3 depicts the temperature and concentration-dependent sol-gel transition of F127 and F127-BPEI.
Figure 4:
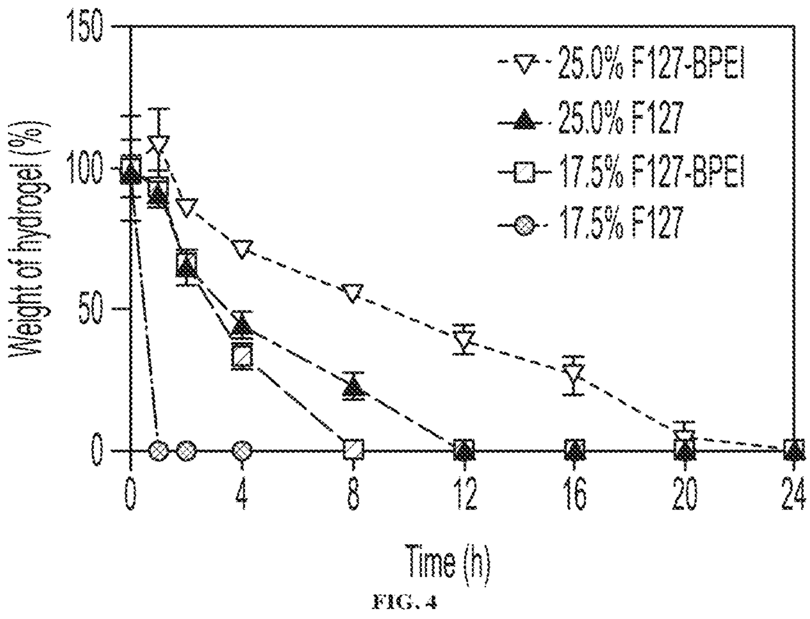
FIG. 4 depicts the stability of F127 and F127-BPEI hydrogel in DMEM containing 10% FBS.
Figure 5:
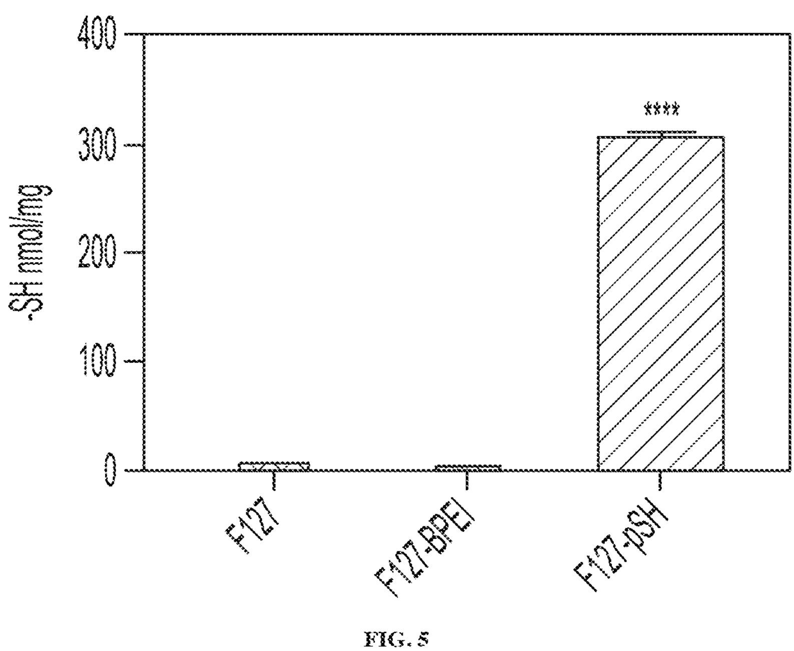
FIG. 5 depicts the quantification of thiol groups in F127, F127-BPEI, and F127-pSH.

Successful conjugation of BPEI in F127-BPEI was demonstrated by 1H NMR by confirming the amine peaks in 2.6-2.9 ppm (FIG. 2). The thermosensitivity of F127 and F127-BPEI was evaluated by vial tilting method. In vitro stability of F127 and F127-BPEI was evaluated by weighing the hydrogels incubated in DMEM containing 10% FBS at 37° C. water bath. F127-BPEI had higher stability than F127 as confirmed by sol-gel transition curves (FIG. 3, Table 1), which would be attributed to the stabilization effects of hydrophilic BPEI in micelle-micelle interaction, as reported previously. However, it was able to retain its structure only for one day (FIG. 4), which justified the needs of in situ crosslinked hydrogels for the sustained immune checkpoint blockade antibodies release in vivo. The secondary and primary amines of F127-BPEI were further converted to thiol groups to afford the F127-pSH by reacting with propylene sulfide (FIG. 1), as confirmed by 1H NMR showing methyl and tertiary proton peaks at 1.2-1.4 and 2.8-3.2 ppm, respectively (FIG. 2). Resultant F127-pSH (100 mg) in PBS without calcium and magnesium (2 mL) was reacted with tris(2-carboxyethyl)phosphine (50 mg) for 30 min to reduce disulfide bonds and then purified by five times centrifugal dialysis with Amicon® ultra-15 centrifugal tube (MWCO 10 kDa). Thiol contents of the reduced F127-pSH were quantified by Ellman's assay. Ellman's assay demonstrated that one F127-pSH contains 4.00±0.04 thiol groups, calculated from the results that one F127-BPEI contains 0.82±0.01 BPEI and 1 mg of resultant F127-pSH contains 305.6±3.3 nmole thiol groups (FIG. 5).

TABLE 1

Sol-gel and gel-sol transition temperature of F127 and F127-BPEI.

| | Sol→gel transition temperature/ Gel→Sol transition temperature | |
|---|---|---|
| Wt % | F127 | F127-BPEI |
| 1 | Not available (N.A.) | N.A. |
| 5 | N.A. | N.A. |
| 10 | N.A. | N.A. |
| 15 | N.A. | 26° C./62° C. |
| 17.5 | 36° C./48° C. | 24° C./65° C. |
| 20 | 24° C./64° C. | 22° C./69° C. |
| 25 | 22° C./76° C. | 20° C./98° C. |

Example 2—Preparation and Characterization of In Situ Crosslinked Hydrogel (F127/PEG)

Figures 6A, 6B, 6C, 6D, 6E, 6F:
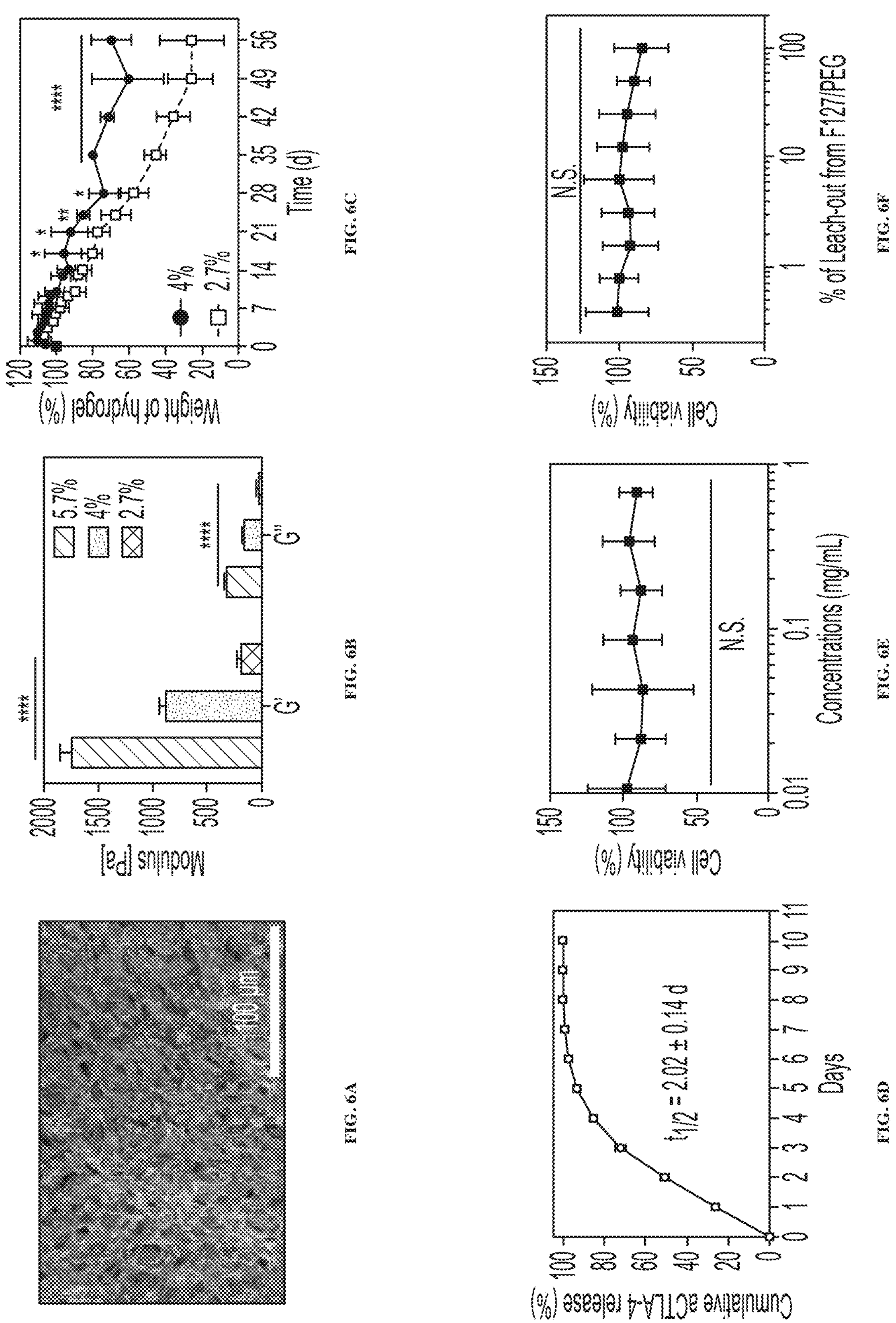
(FIG. 6A) SEM images of F127/PEG hydrogel.
(FIG. 6B) Rheology of F127/PEG hydrogels.
(FIG. 6C) In vitro stability of F127/PEG hydrogels.
(FIG. 6D) In vitro antibody (Alexa Fluor™ 647 labelled aCTLA-4) release from 2.7% F127/PEG hydrogels.
(FIG. 6E) Cytotoxicity of F127/PEG polymers on NIH3T3 cells.
(FIG. 6F) Cytotoxicity of F127/PEG hydrogel leach-out extracts on NIH3T3 cells. **$p<0.0001$, *$p<0.001$, **$p<0.01$, and *$p<0.05$, which were analyzed with one-way ANOVA for (B), (E), and (F), and two-way ANOVA test for (C).

2.7 wt. % F127/PEG hydrogel was formed by mixing 4% (w/v) reduced F127-pSH (8 μL in PBS without calcium and magnesium), antibodies containing PBS (16 μL in PBS with calcium and magnesium) and 8% (w/v) 4-arm PEG-Maleimide (MW 20 kDa) (6 μL in PBS without calcium and magnesium) at a molar ratio of 1:1 thiol to maleimide. The F127/PEG hydrogel was formed in 10 s (total hydrogel volume=30 μL in 2.7% hydrogel) to 1 min (total hydrogel volume=1 mL in 2.7% hydrogel) after mixing the solution. Scanning electron microscopy (SEM) images were obtained from lyophilized hydrogel by using hitachi SU-8230 at accelerating voltage 1 kV and 10 μA emission current. The hydrogel exhibited porous structures, as revealed in SEM images (FIG. 6A). Rheological properties of hydrogel were investigated by dynamic oscillatory strain and frequency sweeps on a Discovery HR-2 rheometer (TA Instruments) with an 8 mm diameter, flat geometry at an angular frequency (ω) of 1-10 rad $s^{-1}$ (Plate SST 8 mm Smart-Swap, TA Instruments). Hydrogel with higher polymer concentrations resulted in higher measured storage (G') and loss moduli (G") by rheology (FIG. 6B). In vitro stability of hydrogels was evaluated by weighing the hydrogel incubated in DMEM containing 10% FBS at 37° C. water bath. 4% polymer weight hydrogels exhibited notable resistances to spontaneous degradation compared to hydrogels formed from 2.7% polymer weights, implying the concentration-dependent modulation of hydrogel stability (FIG. 6C). aCTLA-4 release from hydrogel was observed in Alexa Fluor™ 647 labelled aCTLA-4 containing 90 μL 2.7 wt. % hydrogel incubated in 180 μL PBS at 37° C. water bath. At pre-determined time point, supernatant was collected and fresh 180 μL PBS was added. The fluorescence of supernatants were recorded for the aCTLA-4 release test. As high polymer concentration solutions can be challenging not only to handle but to also form homogenous hydrogels, 2.7% hydrogel was selected for further in vitro and in vivo studies. In vitro, the F127/PEG hydrogel exhibited the sustained release of antibody (t112=2.0±0.1 d) (FIG. 6D).

Example 3—Cytotoxicity Test of F127/PEG

NIH3T3 was seeded onto the 96-well plates at a density of $1\times10^4$ cells/well and then incubated overnight. Polymer solutions were prepared by reacting F127-pSH and 4-arm PEG-mal to be their final concentrations 1 mg/mL in 10% FBS containing DMEM. The polymer solutions with serial dilution were added to the seeded cells and incubated for 2 d. In order to investigate the cytotoxicity of leach-out byproduct of hydrogel, 100 μL hydrogel was formed in 96-well plates and 100 μL 10% FBS containing DMEM was added, followed by 2 d incubation. The supernatants were transferred to the NIH3T3 seeded 96-well plates and incubated for 2 d Alamarblue assay was conducted to evaluate the cytotoxicity of the polymer and leach-out byproducts. Fluorescence signal from cells incubated with 10% FBS DMEM lacking polymers was used to represent the 100% cell viability. Suggestive of favorable biocompatibility of the F127/PEG hydrogel, the polymer components comprising F127/PEG hydrogel also did not induce any cytotoxicity on a mouse fibroblast cell line (NIH3T3) up to 1 mg/mL (FIG. 6E) and the leach-out extract from hydrogel exhibited negligible cytotoxicity to NIH3T3 (FIG. 6F).

Figures 7A, 7B, 7C:
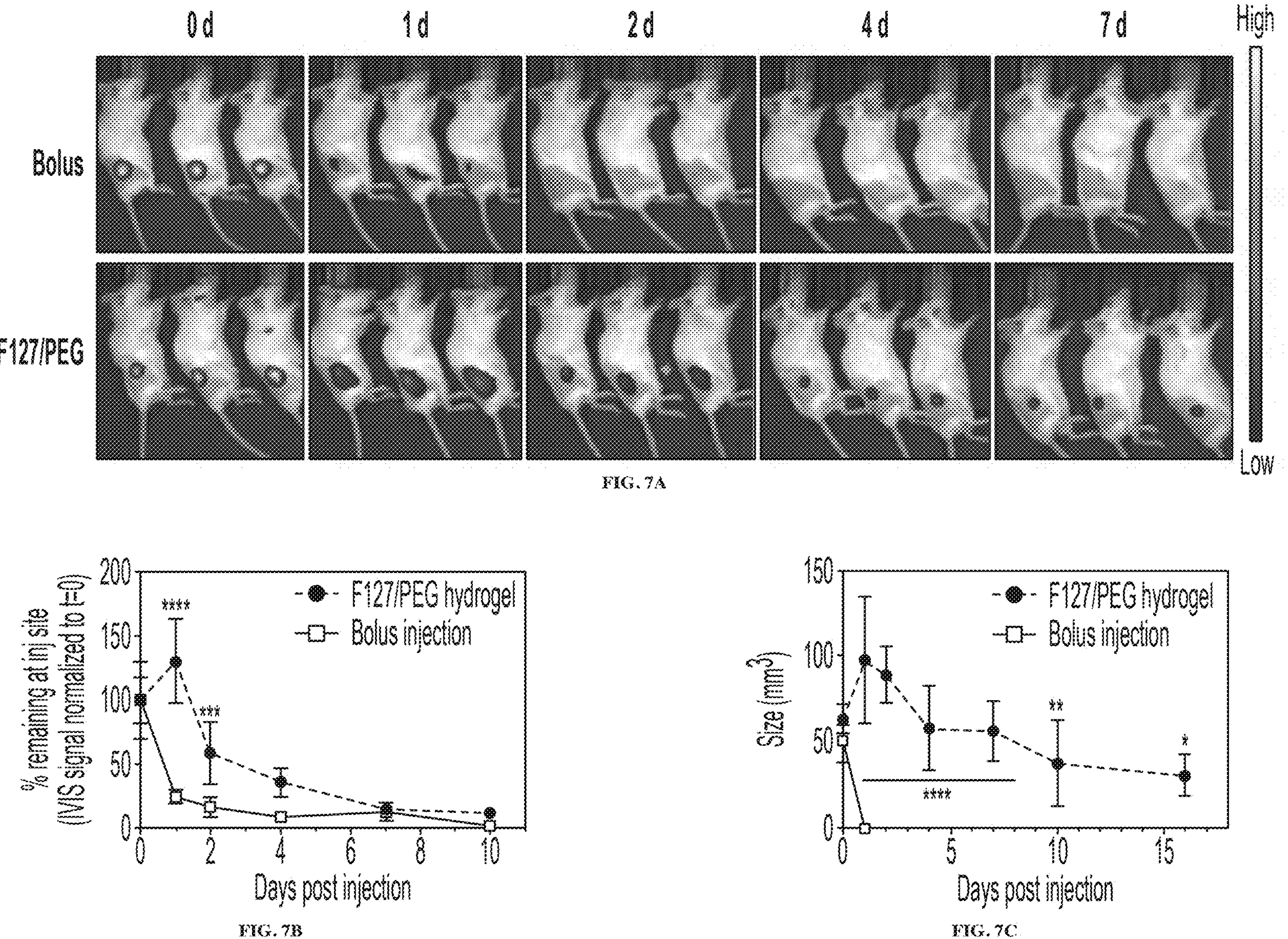
(FIG. 7A) Time-resolved IVIS images of Alexa Fluor™ 647 labelled aCTLA-4 antibody dermally injected with bolus or within 2.7% F127/PEG hydrogels.
(FIG. 7B) Quantification of IVIS fluorescence at injection site.
(FIG. 7C) In vivo stability of F127/PEG hydrogels. **$p<0.0001$, *$p<0.001$, **$p<0.01$, and *$p<0.05$, which were analyzed with two-way ANOVA test.

Example 4—In Vivo Stability of F127/PEG Hydrogel and aCTLA-4 Release Test from the Hydrogel Whether F127/PEG hydrogels facilitate the sustained release of immune checkpoint blockade antibodies in vivo was next investigated. IACUC approved all animal experiments that were performed in the PRL at the Georgia Institute of Technology. In vivo aCTLA-4 release was evaluated by measuring fluorescence where 30 μL of 2.7 wt. % hydrogel containing Alexa Fluor™ 647 labelled aCTLA-4 was injected, which was quantified with an IVIS® Spectrum instrument (Perkin Elmer, MA, USA). High fluorescent signal was found to be sustained only in animals in which fluorescent antibody was delivered in F127/PEG hydrogels. While less than half of aCTLA-4 antibody (25.0±2.2%) injected as a bolus remained after one day, antibody signal within F127/PEG hydrogels was detectable over the entire seven days and exhibited significantly longer half-life (3.3±0.4 d) (FIG. 7A, B). Considering that dense hydrogel structures reduce the diffusion of water and drugs, sustained drug release is generally dependent on the stability of hydrogel. In vivo stability of F127/PEG hydrogel was investigated by measuring the size of 30 μL of 2.7 wt. % hydrogel dorsally injected to the Balb/C mouse. Indeed, the F127/PEG hydrogel retained its size during more than two weeks although its size slowly reduced over time (FIG. 7C). Therefore, the significantly prolonged release of immune checkpoint blockade antibodies from F127/PEG hydrogels compared to bolus delivery can be ascribed to the long residence time of F127/PEG hydrogel in vivo.

Figure 8A:
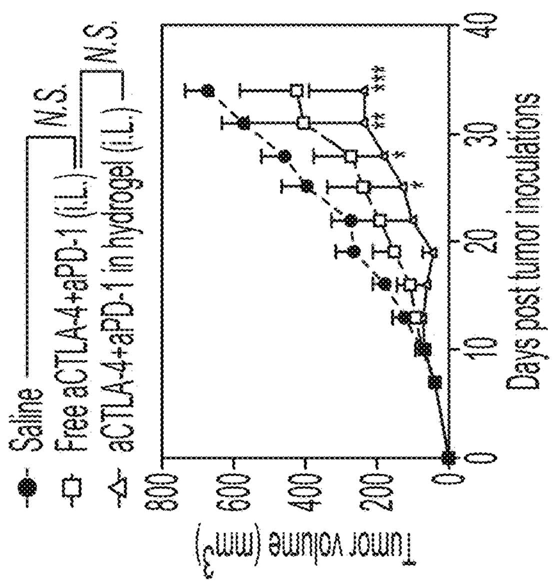
(FIG. 8A) Tumor size after one administration of saline, free aCTLA-4+aPD-1 antibodies, or aCTLA-4+aPD-1 antibody containing F127/PEG hydrogels injected i.d. injected in tissue i.l. to tumor. Arrow indicates administration date.
Figure 8A:
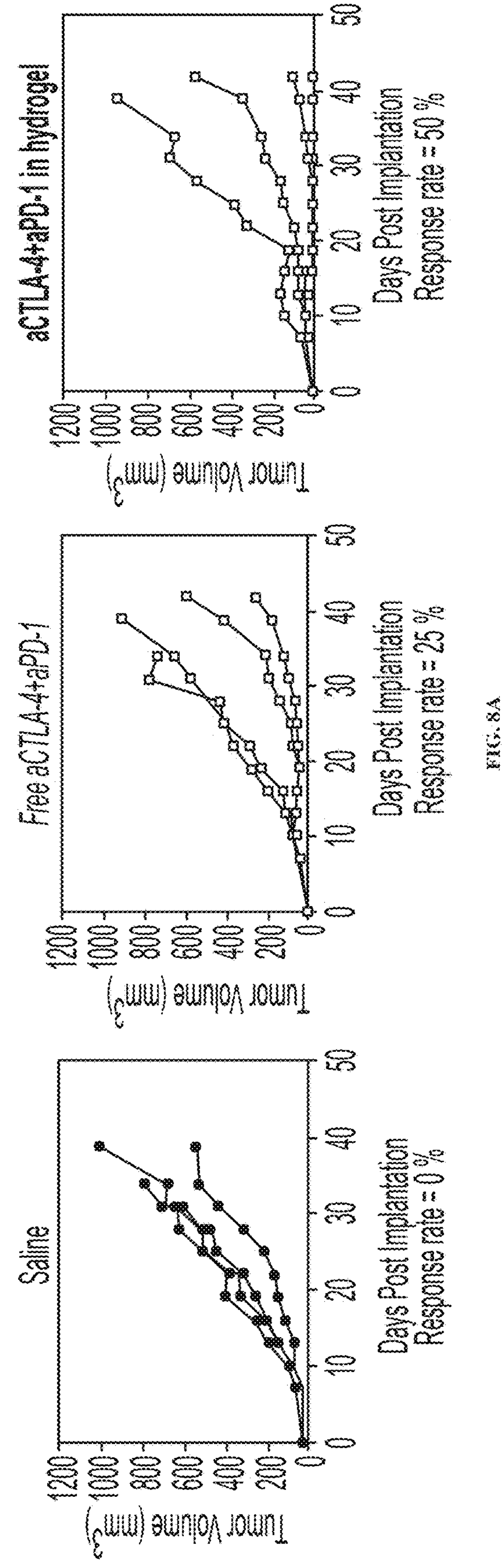
Figure 8B:
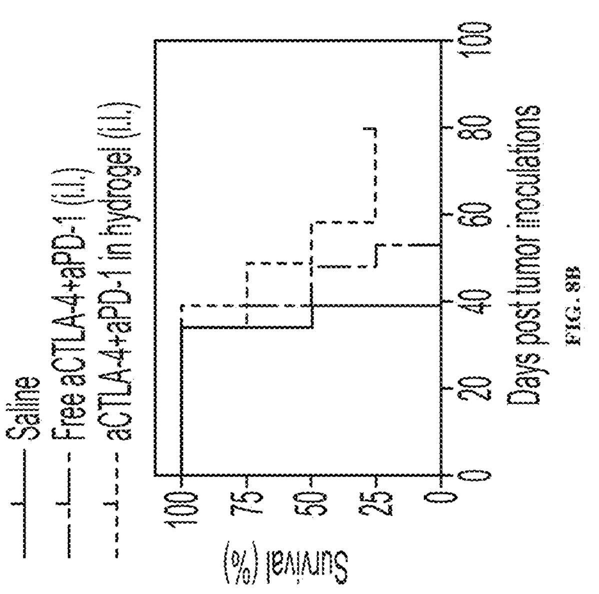
(FIG. 8B) Animal survival curves.
Figure 8C:
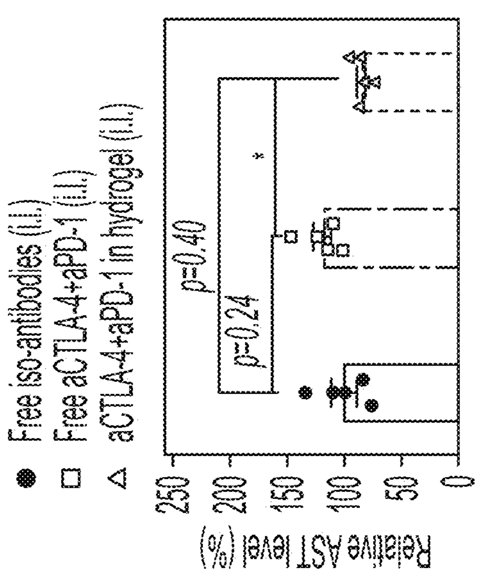
(FIGS. 8C and 8D) ALT/AST in blood 2 d after treatment. * in (A) indicates statistical differences compared with saline and aCTLA-4+aPD-1 antibody containing hydrogels, analyzed with two-way ANOVA. (C) and (D) were analyzed with one-way ANOVA.
Figure 8D:
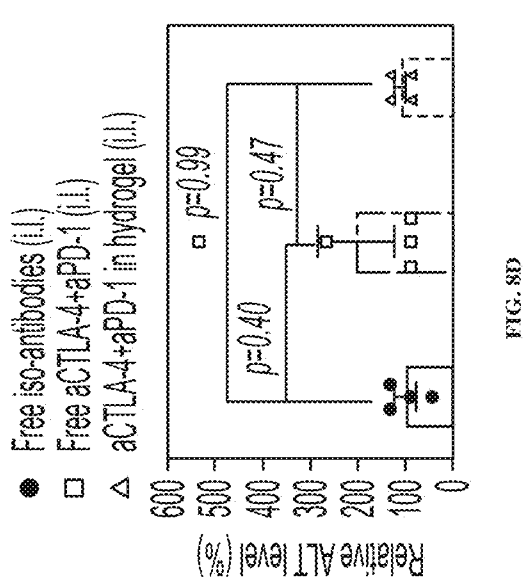
Figure 9:
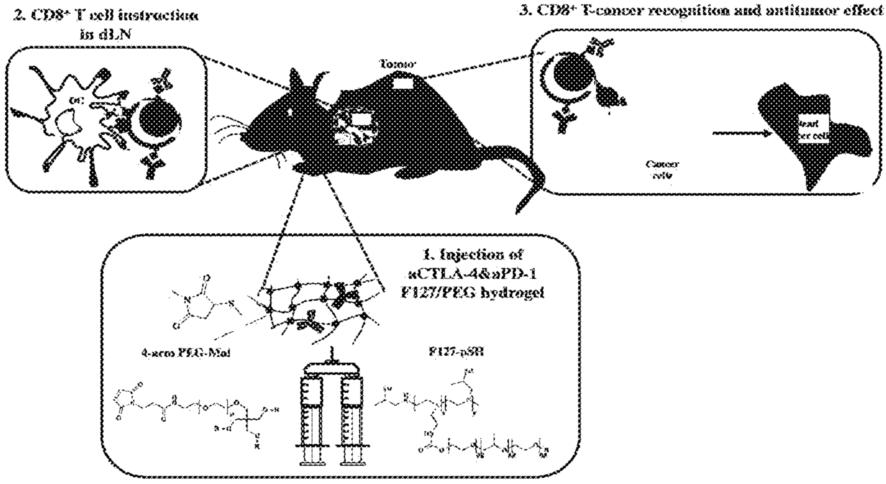
FIG. 9 depicts a schematic of the immune checkpoint blockade (ICB) antibody releasing hydrogel for antitumor therapy. ICB antibodies are released from intradermally injected hydrogels in a sustained manner. As a result, the benefits of ICB for T cell instruction are prolonged, improving the anti-tumor effects of ICB immunotherapy (the chemical structure does not depict the crosslinked amphiphilic polymers present).

Example 5—In Vivo Anticancer Therapy with aCTLA-4 and aPD-1 Releasing F127/PEG Hydrogel In order to investigate the effects of sustained release of immune checkpoint blockade antibodies in anticancer therapy, 4T1 murine breast tumor model was selected a model of metastatic triple negative breast cancer. In detail, IACUC approved all animal experiments that were performed in the PRL at the Georgia Institute of Technology. $3\times10^5$ 4T1 cells were inoculated intradermally in the left mammary fatpad of 6-12 week old Balb/C mice on day 0. 30 μL of saline, free aCTLA-4+aPD-1, and aCTLA-4&aPD-1 containing F127/PEG hydrogel (dose equivalent to 50 μg of each aCTLA-4 and aPD-1) was administered to the skin ipsilateral to the tumor (i.l.) on day 10. Blood serum was collected 2 d after treatments, which was further analyzed with ALT and AST assay kit to investigate the systemic liver toxicity. The survival curves were depicted by Kaplan-Meier curves. Tumor volume was calculated by the formula: a×b×c, where a is the width, b is the height, and c is the thickness, respectively. aCTLA-4+aPD-1 antibody containing F127/PEG hydrogels showed improved therapeutic effects compared to control groups (FIG. 8A). The response rate of aCTLA-4+aPD-1 antibody containing F127/PEG hydrogels was 50%, while that of free aCTLA-4+aPD-1 antibody was 25%. In addition to reduced tumor growth, significantly prolonged survival (FIG. 8B) was observed in aCTLA-4+aPD-1 antibody containing F127/PEG hydrogels compared to control groups. Additionally, aCTLA-4+aPD-1 antibody containing F127/PEG hydrogels had negligible effects on systemic liver toxicity, whereas treatment with free aCTLA-4+aPD-1 antibody resulted in slightly elevated serum alanine and aspartate aminotransferase levels (ALT and AST, respectively), which are indicative of liver toxicity (FIG. 8C, D). Improved therapeutic efficacy and negligible systemic toxicity resulting from treatment with aCTLA-4+aPD-1 antibody containing F127/PEG hydrogels compared to control groups may therefore be attributed to both the prolonged bioavailability of immune checkpoint blockade antibodies in draining lymph node and reduced levels within systemic tissues afforded by the hydrogel formulation (FIG. 9). Therefore, overall results demonstrated that the sustained release of immune checkpoint blockade antibodies by the crosslinked hydrogel leads to improved therapeutic outcomes with negligible systemic toxicity.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A hydrogel composition, comprising a thiolated thermosensitive polymer crosslinked with an electrophilic polymer;

wherein the thiolated thermosensitive polymer is prepared by i) conjugating an amphiphilic polymer with a polymer having at least three primary amine groups to provide an intermediate polymer, and ii) thiolating said intermediate polymer to provide the thiolated thermosensitive polymer;

wherein, prior to crosslinking with the thiolated thermosensitive polymer, the electrophilic polymer has the formula:

[Formula (1)]

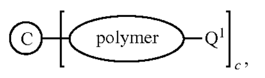

wherein the encircled C represents a core, the encircled polymer represents a hydrophilic polymer, c is an integer selected from 3, 4, 5, 6, 7, 8, 9, or 10, and $Q^1$ is an electrophilic group.

2. The hydrogel composition according to claim 1, further comprising one or more therapeutic agents.

3. The hydrogel composition according to claim 2, wherein the therapeutic agent comprises an immune checkpoint blockade antibody, an antibiotic, a vaccine, a chemotherapeutic, or a combination thereof.

4. The hydrogel composition according to claim 2, wherein the therapeutic agent comprises an anti-CTLA-4 antibody, an anti-PD-1 antibody, or a combination thereof.

5. The hydrogel composition according to claim 2, wherein the therapeutic agent is an immune checkpoint blockade antibody and an anticancer agent.

6. The hydrogel according to claim 1, wherein the polymer having at least three primary amine groups is polyethyleneimine, polypropyleneimine, or combination thereof.

7. The hydrogel according to claim 1, wherein the polymer having at least three primary amine groups is polyethyleneimine having a molecular weight from 250-1,000.

8. The hydrogel according to claim 1, wherein the amphiphilic polymer comprises a poly(ethylene oxide)-poly(propylene oxide) block copolymer.

9. The hydrogel according to claim 8, wherein the poly (ethylene oxide)-poly(propylene oxide) block copolymer is a compound of Formula (2a) or (2b):

[Formula (2a)]

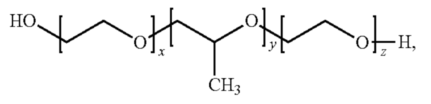

[Formula (2b)]

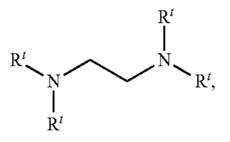

wherein $R^1$ is in each case:

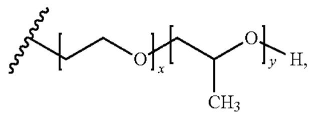

wherein x, y, and z are independently selected from 5-500.

10. The hydrogel according to claim 9, wherein y is from 50-70, and x and z are independently selected from 75-125.

11. The hydrogel according to claim 1, wherein the molar ratio of amphiphilic polymer to polymer having at least three primary amine groups is from 10:1 to 1.05:1.

12. The hydrogel according to claim 1, wherein the hydrophilic polymer is polyethylene glycol.

13. The hydrogel according to claim 4, wherein encircled C has the formula:

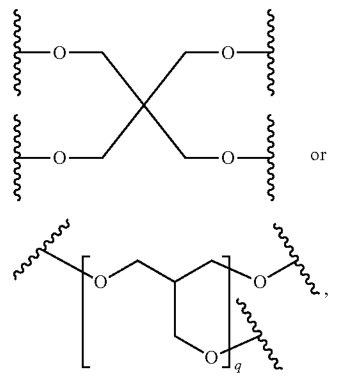

wherein q is 1, 2, or 3.

14. The hydrogel according to claim 5, wherein $Q^1$ has the formula:

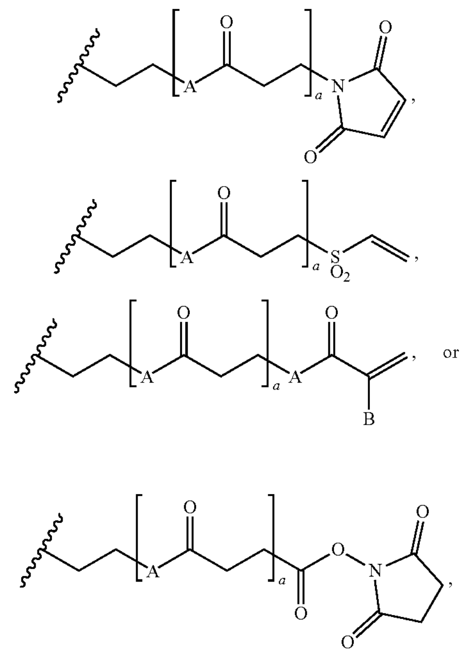

wherein A is independently selected from O or NH, a is independently selected from 0 or 1, B is selected from hydrogen or methyl, and ⌇ represents a link to the hydrophilic polymer.

15. The hydrogel composition according to claim 6, wherein the thiolated thermosensitive polymer has from 1-20 thiol groups.

16. The hydrogel composition according to claim 7, wherein the electrophilic polymer is combined with the thiolated thermosensitive polymer in an aqueous vehicle, wherein the molar ratio of thiol to $Q^1$ groups is 1.5:1 to 1:1.5.

17. A method of making a hydrogel composition, the method comprising crosslinking an electrophilic polymer with a thiolated thermosensitive polymer;

wherein the electrophilic polymer has the formula:

[Formula (1)]

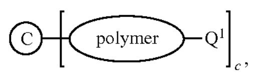

wherein the encircled C represents a core, the encircled polymer represents a hydrophilic polymer, c is an integer selected from 3, 4, 5, 6, 7, 8, 9, or 10, and $Q^1$ is an electrophilic group.

18. The method of claim 17, further comprising i) conjugating an amphiphilic polymer with a polymer having at least three primary amine groups to provide an intermediate polymer, and ii) thiolating said intermediate polymer to provide the thiolated thermosensitive polymer.

19. The method of claim 18, wherein step ii) comprises reacting the intermediate polymer with propylene sulfide to provide the thiolated thermosensitive polymer.

20. A method of treating cancer in a patient in need thereof, the method comprising administering to the patient the hydrogel composition according to claim 3.

* * * * *